United States Patent
Okamura

(10) Patent No.: US 8,120,654 B2
(45) Date of Patent: Feb. 21, 2012

(54) DEVICE AND METHOD FOR DETECTING DEFECT ON END FACE OF GLASS SHEET

(75) Inventor: Shinichi Okamura, Mie (JP)

(73) Assignee: Central Glass Co., Ltd., Yamaguchi (JP)

( * ) Notice: Subject to any disclaimer, the term of this patent is extended or adjusted under 35 U.S.C. 154(b) by 1015 days.

(21) Appl. No.: 11/884,142

(22) PCT Filed: Feb. 10, 2006

(86) PCT No.: PCT/JP2006/302371
§ 371 (c)(1),
(2), (4) Date: Mar. 12, 2008

(87) PCT Pub. No.: WO2006/085618
PCT Pub. Date: Aug. 17, 2006

(65) Prior Publication Data
US 2010/0149327 A1    Jun. 17, 2010

(30) Foreign Application Priority Data
Feb. 10, 2005    (JP) .............................. P 2005-034238

(51) Int. Cl.
*H04N 7/18*    (2006.01)
(52) U.S. Cl. ............................ 348/131; 348/92; 348/127
(58) Field of Classification Search .................... 348/86, 348/92, 125, 127, 131
See application file for complete search history.

(56) References Cited

U.S. PATENT DOCUMENTS

| | | | | |
|---|---|---|---|---|
| 5,680,217 A | * | 10/1997 | Yli-Vakkuri | 356/602 |
| 6,118,524 A | * | 9/2000 | King et al. | 356/237.1 |
| 6,154,561 A | * | 11/2000 | Pratt et al. | 382/141 |
| 6,359,686 B1 | * | 3/2002 | Ariglio et al. | 356/239.1 |
| 6,501,546 B1 | * | 12/2002 | Weiss | 356/239.1 |
| 7,345,698 B2 | * | 3/2008 | Abbott et al. | 348/86 |
| 7,420,671 B2 | * | 9/2008 | Sonda | 356/239.1 |

(Continued)

FOREIGN PATENT DOCUMENTS

CH    681748    5/1993

(Continued)

OTHER PUBLICATIONS

European Search Report—EP 06 71 3514—Oct. 24, 2011.

*Primary Examiner* — Patrice Winder
(74) *Attorney, Agent, or Firm* — Young & Thompson

(57) ABSTRACT

A device for detecting a defect on the end face of a glass sheet is provided with: an image pick-up device having at least two CCD cameras for image-picking up the end face of the glass sheet from outside the glass sheet and in two directions diagonal to both front and back surfaces thereof; an illuminating device having a nearly C-shaped ring illumination capable of applying illuminating light in its center axis direction and having an opening slit; and an image processing device for processing the image signals acquired from the CCD cameras to determine the quality of the end face. The glass sheet is loosely inserted in the opening slit so that the end face agrees with the center axis of the ring illumination; the illuminating light is applied to the end face; and the end face is image-picked up by the image pick-up device. The image signals thus acquired are processed by the image processing device, thereby detecting the presence/absence of the defect on the end face.

14 Claims, 10 Drawing Sheets

U.S. PATENT DOCUMENTS

| | | | |
|---|---|---|---|
| 2002/0196338 A1 * | 12/2002 | Tham | 348/131 |
| 2008/0225115 A1 * | 9/2008 | Matsushita | 348/129 |

FOREIGN PATENT DOCUMENTS

| | | |
|---|---|---|
| JP | 55006214 A  * | 1/1980 |
| JP | 02099806 A  * | 4/1990 |
| JP | 6-258231 | 9/1994 |
| JP | 2001-153816 A | 6/2001 |
| JP | 2003-98122 A | 4/2003 |
| JP | 2003-247953 A | 9/2003 |
| TW | 200300493 | 5/2005 |
| WO | 03/044507 A1 | 5/2003 |

* cited by examiner

DEVICE AND METHOD FOR DETECTING DEFECT ON END FACE OF GLASS SHEET

TECHNICAL FIELD

The invention relates to a device and method for detecting various defects on an end face of a glass sheet and at a boundary line between a ground face and a glass face thereof, which is ground in its end face roundly in an arc or has a seaming area, particularly the defect called a scratch, a shell-shaped chip (hereinafter simply referred to as "shell"), a chip, omission of polishing, non-polishing, or a stain.

BACKGROUND ART

The glass sheet which is molded and transferred in its ribbon shape is kept in a keeping container such as a palette or shipped in a state where it is cut in a square shape and a desired size. In this case, according to a using purpose, an end face edge of the glass sheet after cut is chamfered (seaming) using e.g. a diamond wheel, or otherwise the end face is polished so that the end face becomes an arc-shape in section thereby providing a semi-transparent polished glass. As a result, occurrence of injury in handling the glass sheet is prevented, thereby assuring safety. Further, damaging or reduction in a product value due to reduction in the end face of the glass sheet can be prevented.

Where such seaming processing or end-face processing is executed, as the case may be, at the edge of the glass sheet, the scratch or chip may be generated owing to poor polishing or blocking resulting from abrasion of a diamond wheel.

Particularly, in a process for manufacturing a glass sheet used as a display substrate for a flat display panel for e.g. a liquid crystal display, plasma display, field-emission display, or organic EL display, if there is a fine scratch or chip in the seaming area of the end face of the glass sheet when the glass sheet is heat-treated at a high temperature, a trouble of cracking of the glass sheet may occur.

There are various disclosed techniques for detecting the defect on the end face of the glass sheet. For example, JP-A-2001-153816 discloses a method for detecting an edge defect on a glass sheet in which with the edge of the glass sheet polished after cut is being placed between a light source and a camera, incident light is applied to the edge from the light source to light up the defect at the edge, and the defect is image picked up by the camera, the image thus acquired is processed to investigate the presence/absence of the defect. The light source is arranged behind the glass sheet when seen from the camera so that it is outside the visual field of the camera. The quantity of light which reaches the camera from the light source is limited so that the surface of the glass sheet and the common face of the edge in the image is dark and the chip residing at the edge is bright, thereby optically detecting the chip.

Further, JP-A-06-258231 filed by the applicant of this application discloses a device for detecting the defect at an edge of a glass sheet having a seaming face chamfered at the edge in a state where it is placed horizontally. This detecting device includes a light source for emitting light to the edge from two upper and lower diagonal directions on the side opposite to the glass sheet, and at least two cameras for picking up the edge at the corner on the light source side of the glass sheet face and seaming face, through a transparent area of the glass sheet, from outside the extended area of an optical path of the light applied to the edge and the side opposite to the light emitting direction. The defects at the edge are discriminated by the magnitude of the bright signal acquired from image-pick-up by the cameras.

Further, JP-A-2003-247953 discloses a method and device for checking the external appearance of a liquid crystal panel. In the device for checking the external appearance of the liquid crystal panel, a ring illuminating lamp having a diameter larger than the external size of the liquid crystal panel is arranged on the outer periphery of the liquid crystal panel. The method for checking the external appearance of the liquid crystal panel includes a step of arranging an image pick-up device just above the liquid crystal panel; a step of applying illuminating light from the ring illuminating lamp turned on toward the end face of the liquid crystal panel and image-picking up, by the image pick-up device, the light reflected from the side of the liquid crystal panel illuminated with the illuminating light; binary-digitizing, by an image processing device, the image picked up by the pick-up device, detecting the external shape of the liquid crystal panel on the basis of a frame-like white image appeared in the image and detecting the chip or crack of the end face of the liquid crystal panel from the presence/absence from the other white image.

In the defect detecting method disclosed in the above JP-A-2001-153816, the bottom face of the glass sheet is illuminated by the illumination from a lower-longitudinal direction to the rounded end face of the glass sheet so that only the chip appearing at the edge of the glass sheet shines and the other area of the glass sheet becomes completely dark. Thus, of various defects, the shining chip can be detected, but other defects such as the scratch, non-polishing or stain cannot be detected.

Further, in the device disclosed in JP-A-06-258231, illuminating light is applied, from two diagonal upper and diagonal lower directions, to the seaming area diagonally grinding-cut at the ridgeline of the edge of each both the front and back faces of the glass sheet. Therefore, the scratch or stain in the seaming area of the glass sheet can be detected to a certain extent. However, in the process for manufacturing the glass sheet of a flat display panel having the rounded end face, for e.g. the liquid crystal display or plasma display, the glass sheet is heat-treated at a high temperature so that the fine scratch or chip existing at the end face or seaming area of the glass sheet may probably lead to the crack of the glass sheet. Therefore, in the step of manufacturing the glass sheet of the flat display panel, fine defects including chip, non-polishing as well as the scratch and stain must be detected more sophisticatedly than in the device disclosed in JP-A-06-258231.

Further, in the device and method disclosed in JP-A-2003-247953, the ring illuminating lamp having a diameter larger than the external size of the liquid crystal panel is arranged on the outer periphery of the liquid crystal panel and the camera is arranged above the center of the liquid crystal panel. In this arrangement, the scratch, crack and chip on the surface of the liquid crystal panel and the crack and chip on the end face are simultaneously checked. Therefore, the ring illuminating lamp must be changed according to changes in the size of the liquid crystal panel.

In addition, since the liquid crystal panel is generally square and the ring-shaped illuminating lamp is arranged on the outer periphery thereof, the interval between the liquid crystal panel and the ring illumination is not constant. Thus, the intensity of the illumination on the end face of the liquid crystal panel is not constant.

Further, the ring illumination is upsized according to upsizing of the liquid crystal panel so that the facility will be inevitably upsized. Since the camera is provided only above the center of the liquid crystal panel, the angle of image-picking up the end face changes. Thus, as the case may be, the fine defect on the end face such as the scratch, omission of polishing, non-polishing or stain cannot be detected accurately.

Further, where the entire periphery of the end face of the glass sheet is polished in a rounded shape, if the ring illumination is arranged on the one side of the glass sheet and the area from the center to the end face is image-picked up, the end face will shine partially greatly. So, it was difficult to make the intensity of the illumination on the end face uniformly constant. It was also difficult to detect the defects on the end face and at the boundary line between the polished face and glass face by the same optical system.

DISCLOSURE OF THE INVENTION

One or more embodiments of the invention provide a method and device for detecting defects on a glass sheet, which can simultaneously detect, surely and accurately, various defects such as a scratch, a chip, omission of polishing, non-polishing, or a stain on the rounded end face of the glass sheet for a flat display panel for e.g. a liquid crystal display, plasma display, field emission display or organic EL display, and further can detect the "shell" or chip at the boundary line between the end face rounded by grinding or polishing and both upper and lower surfaces of the glass sheet.

In accordance with one or more embodiments of the invention, the device for detecting a defect on the end face of a glass sheet is provided with: an image pick-up device having at least two CCD cameras for image-picking up the end face of the glass sheet from outside the glass sheet and in two directions diagonal to both front and back surfaces thereof; an illuminating device having a nearly C-shaped ring illumination capable of applying illuminating light in its center axis direction and having an opening slit; and an image processing device for processing the image signals acquired from the CCD cameras to determine the quality of the end face. The glass sheet is loosely inserted in the opening slit so that the end face agrees with the center axis of the ring illumination; the illuminating device applies the illuminating light to the end face; and the image signals acquired from image-pick-up of the end face by the image pick-up device are processed by the image processing device, thereby detecting the defect on the end face.

Additionally, in accordance with one or more embodiments of the invention, the glass sheet may have the end face which is chamfered to constitute an arc-shaped end face or a smooth ridge.

Additionally, in accordance with one or more embodiments of the invention, the illuminating device may two C-shaped illuminations arranged in the vicinity of both right and left sides of the area to be defect-inspected of the end face of the glass sheet. The area to be defect-inspected is illuminated by each of the illuminations.

Additionally, in accordance with one or more embodiments of the invention, the illuminating device may have diffusive/permeable light sources for applying illuminating light to the end face of the glass sheet from two directions diagonal to both front and back surfaces of the glass sheet.

Additionally, in accordance with one or more embodiments of the invention, the ring illumination may have a plurality of LED elements arranged concentrically.

Additionally, in accordance with one or more embodiments of the invention, the device for detecting a defect on the end face of a glass sheet, further includes a carrying device for carrying the glass sheet so that the sides of the glass sheet are in parallel to a carrying direction. The illuminating device and the image pick-up device are arranged in the vicinity of the end face of each of both sides of the glass sheet, respectively.

Additionally, in accordance with one or more embodiments of the invention, the illuminating device and the image pick-up device may be attached to the hand of a robot. The hand may be sequentially moved along the end face on the outer periphery of the glass sheet so that the end face of the glass sheet is image-picked up and the image signal thus acquired are sequentially processed by the image processing device.

Additionally, in accordance with one or more embodiments of the invention, the device for detecting a defect on the end face of a glass sheet can include a first defect inspecting device for inspecting the end face of a side in parallel to the carrying direction of the glass sheet being carried, the first defect inspecting device being fixed for carrying; and a second defect inspecting device for inspecting the end face of the side perpendicular to the carrying direction of the glass sheet being carried, the second defect inspecting device being movable for the glass sheet. The first defect inspecting device and the second inspecting device are provided with the illuminating device and the image pick-up device, respectively.

Additionally, in accordance with one or more embodiments of the invention, a method for detecting a defect on the end face of a glass sheet is provided with the steps of: loosely inserting the end face of a glass sheet into an opening slit of a ring illumination formed in a C-shape; applying illuminating light of the ring illumination to an area of the end face to be inspected where the position of the end face and the center axis of the ring illumination overlap; image-picking up the end face by two CCD cameras; comparing the gray level of the image signal acquired by image-picking up with two upper and lower limit levels previously set; and detecting the presence/absence and kind of the defect according to the position, size and shape of a pixel signal higher than the upper limit level or lower than the lower limit level.

Additionally, in accordance with one or more embodiments of the invention, the method for detecting a defect on the end face of a glass sheet is further provided with the steps of: carrying the glass sheet by a carrying device so that a side of the glass is in parallel to a carrying direction thereof; arranging at least an illuminating device having the C-shaped ring illumination and an image pick-up device for image-picking up the end face illuminated by the illuminating device, in the vicinity of the end face of each of both sides of the glass sheet, respectively; processing the image signal of the end face image-picked up by the image pick-up device by an image processing device; and detecting the presence/absence of the defect.

Additionally, in accordance with one or more embodiments of the invention, the method for detecting a defect on the end face of a glass sheet is further provided with the steps of: attaching, to the hand of a robot, at least an illuminating device having the C-shaped ring illumination and an image pick-up device for image-picking up the end face illuminated by the illuminating device; sequentially the hand along the end face of the outer periphery of the glass sheet; image-picking up the end face of the glass sheet; sequentially processing the image signal thus acquired by an image processing device, and detecting the presence/absence of the defect.

Additionally, in accordance with one or more embodiments of the invention, the method for detecting a defect on the end face of a glass sheet is further provided with the steps of: inspecting the end face of a side in parallel to the carrying direction of the glass sheet being carried by a first defect inspecting device being fixed for carrying; and inspecting the end face of the side perpendicular to the carrying direction of the glass sheet being carried, the second defect inspecting device being movable for the glass sheet. The first defect inspecting device and the second inspecting device are provided with the C-shaped ring illumination and two CCD cameras, respectively.

In accordance with one or more embodiments of the invention, as an arrangement of the light source to be applied to the end of the glass sheet, in place of a conventional arrangement in which the light source is applied at a limited angle of an outer peripheral direction of the glass end face, an upper diagonal or a lower diagonal direction to the end face, the end of the glass sheet is loosely inserted orthogonally in the opening slit of the C-shaped ring illumination so that the end of the glass sheet is located on the center axis of the ring illumination. For this reason, the light source can be uniformly applied to the end face arc-shaped in section from the upper surface to the lower surface of the glass sheet. In such an illuminating arrangement, the end uniformly illuminated with the illuminating light is image-picked up in two directions upper and lower diagonal to the glass sheet by the CCD cameras. Thus, the accuracy of detecting each of the defects such as scratches, chips, omission of polishing, non-polishing and stains can be improved.

Further, a set of permeable illuminations are arranged to be oriented to the end from above and below the glass sheet so that this optical system of the permeable illuminations and the optical system of the ring illumination do not interfere with each other. For this reason, the chips or stains which are generated at the boundaries between the end face arc-shaped by grounding or polishing and the upper and lower surfaces of the glass sheet can be simultaneously detected by the CCD cameras for detecting the end face. This minimizes the space for installing the inspecting device.

Other aspects and advantages of the invention will be apparent from the following description and the appended claims.

Figure 1:
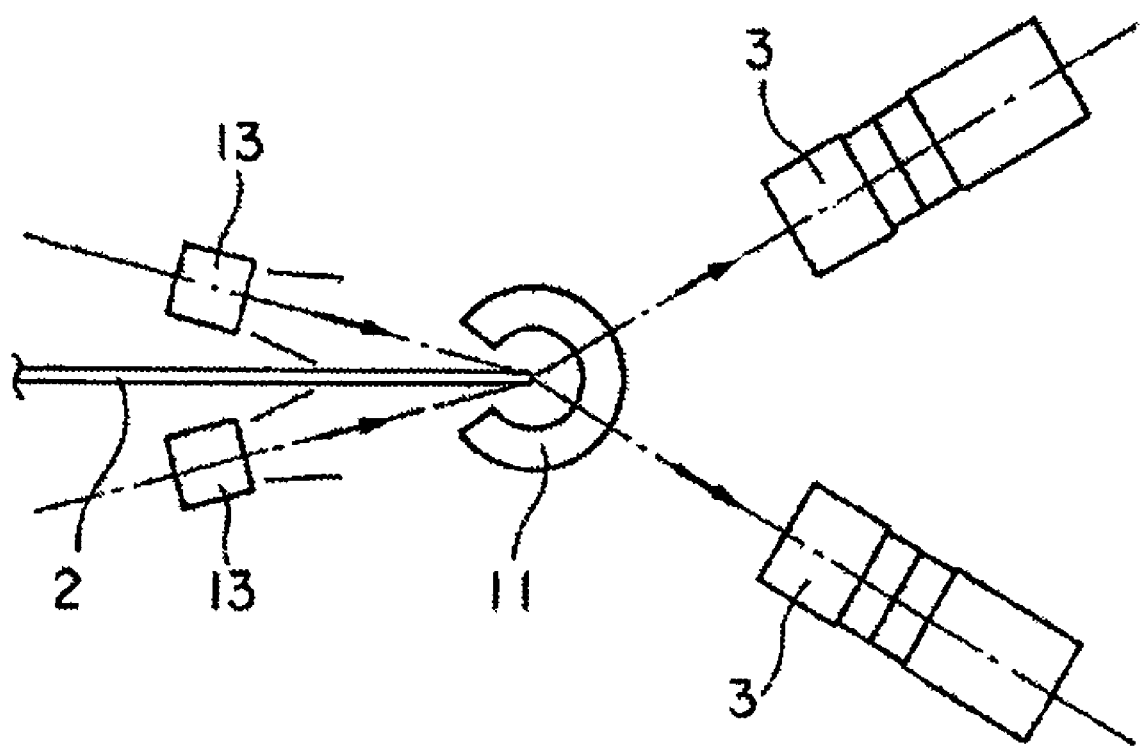
FIG. 1 is a schematic side view showing an arrangement of an illuminating means and an image pick-up means.

DESCRIPTION OF REFERENCE NUMERALS AND SIGNS 1 defect detecting device
2 glass sheet
2a end face
2b ridge (edge)
2c glass face
3 CCD camera
4 image processing means
5 micro-processing device (computer)
6 host computer
8 edge defect
10 illuminating means
11 ring illumination
11a LED element
12 slit
13 diffusive/permeable illumination
20 vertical frame
21 attaching member
22, 23 horizontal frame
24, 25 attaching member
26 transfer line

BEST MODE FOR CARRYING OUT THE INVENTION

An embodiment of the invention provides a device for detecting the defect on the end face in a horizontal state of a glass sheet 2 with the ridge smoothed by grinding or polishing the end face of the glass sheet, or the glass sheet 2 with the sectional shape of the end face being in an arc shape.

Particularly, in the glass substrate for a display such as a liquid crystal display or plasma display, in many cases, the end face of a glass sheet is caused to have a sectional arc-shape which is rounder than a common end face in order to avoid self-destruction under the strict condition of e.g. heating or cooling in the manufacturing process. Therefore, it is necessary to detect the defect by uniformly illuminating the rounded end face with the illuminating light having the shape corresponding to the rounded sectional shape of the end face so that there are no omissions of detection.

The defects to be detected by a defect detecting device 1 according to the invention are a surface defect 8 such as a scratch, chip, omission of polishing and stain which is generated on the rounded end face of the glass sheet, and an edge defect 9 such as a "shell" and crack which is generated in the vicinity of the boundary between the end face rounded by grinding or polishing and the upper or lower surface of the glass sheet.

Of the defects 8, 9, the chip is the edge defect 9 where the edge 2b is literally chipped. The chip is generated in the edge 2b and can have any shape. The defect called "shell" is also the edge defect 9 which is generated in the edge 2b and chipped in a shell-shaped concentrically semispherical arc. The "shell", when it is illuminated with illuminating light by an illuminating device 10, shines white in its entirety (see FIG. 10).

The "scratch" is the surface defect 8 inclusive of a scratch or linear strip. The "stain" is the surface defect 8 which appears whitish in an opaque area of the end face of the glass sheet 2. The stain is generated when the polished face of the glass sheet is molten owing to the frictional heat between a grinding tool and the glass sheet generated during polishing. These defects are generated on the surface of the end face 2a of the glass sheet 2.

The defects of "omission of polishing" and "non-polishing" refers to the areas which have not been polished owing to shortage in polishing or troubles in a polishing device not shown. These defects refer to the surface defect 8 which does not shine white even when they are illuminated with the illuminating light, but their images appears black when they are image-picked up by a camera 3. The defects are generated on only the end face (see FIG. 12).

As seen from FIG. 1, the image pick-up devices each being at least one CCD camera 3 are arranged in two directions outside the end face of the glass sheet 2 and diagonal to the upper and lower faces of the glass sheet 2. The CCD cameras 3, 3 provided in both the upper and lower directions are arranged to image-pick up substantially the same area of the end face of the glass sheet 2.

Where the two CCD cameras are employed as seen from FIG. 1, their attaching angle of the CCD cameras is preferably an angle of about 30 to 45 degrees on the front and back surface sides of the glass sheet with respect to the direction in which the glass sheet face is extended externally. Namely, where the glass sheet is placed horizontally, the desired angle is the angle of 30 to 45 degrees in both the upper and lower directions from the horizontal plane.

Figure 5:
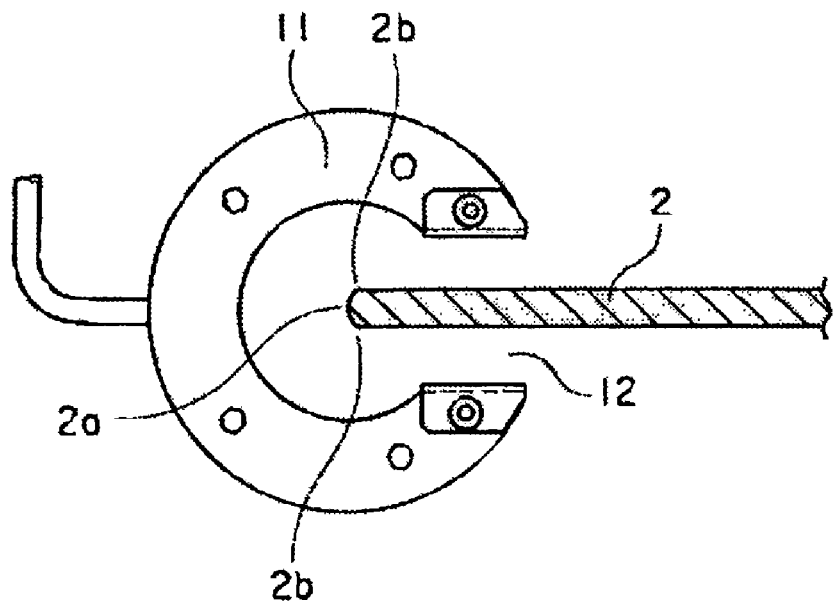
FIG. 5 is a plan view of a ring illumination.

Further, as seen from FIG. 5, a "C"-shaped ring illumination 11 having a slit-like notch is arranged so that the rounded end face 2a at the end of the glass sheet 2 image-picked up by the camera 3 can be illuminated with illuminating light. The end face 2a of the glass sheet 2 is loosely inserted into an opening slit 12 of the ring illumination 11 so that the end face 2a of the glass sheet 2 arc-shaped by grinding or polishing and the center axis of the ring illumination 11 agree with each other. In this state, the illuminating light is emitted from the respective areas of the ring illumination 11 corresponding to the sectional arc-shaped area of the end face 2a. At the end of the glass sheet 2, the plane of the glass sheet 2 and the ring illumination 11 are orthogonal to each other.

In a state where the ring illumination 11 and the glass sheet 2 are arranged, an image processing device 4 (see FIG. 9) is provided which processes the image signals generated from image-pick up of the end face of the glass sheet 2 by at least two CCD cameras 3 to detect the presence/absence of the defect on the end face 2a, thereby determining the quality of the glass sheet.

Figure 2:
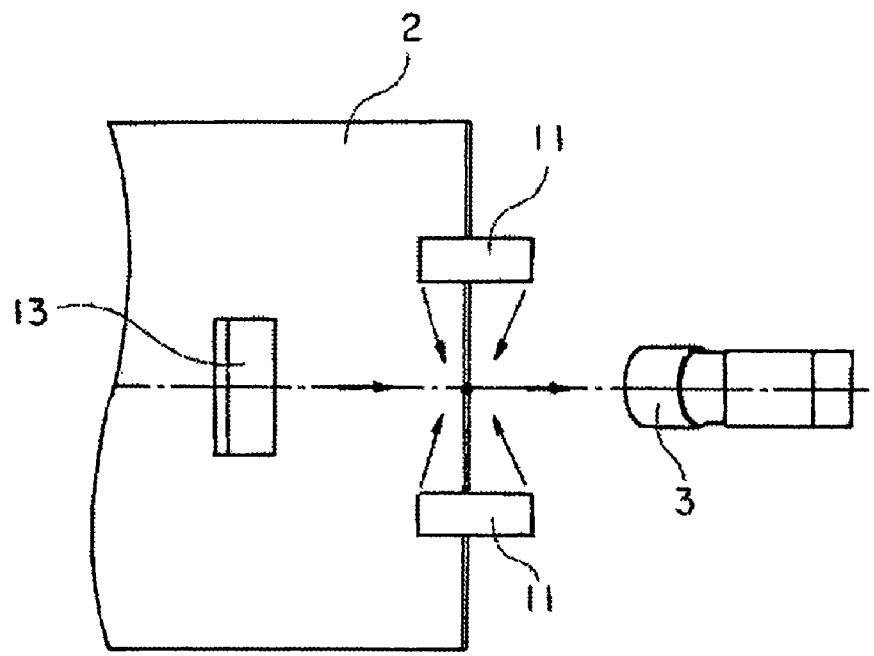
FIG. 2 is a schematic plan view showing an arrangement of an illuminating means and an image pick-up means, in which two ring illuminations are arranged.
Figure 3:
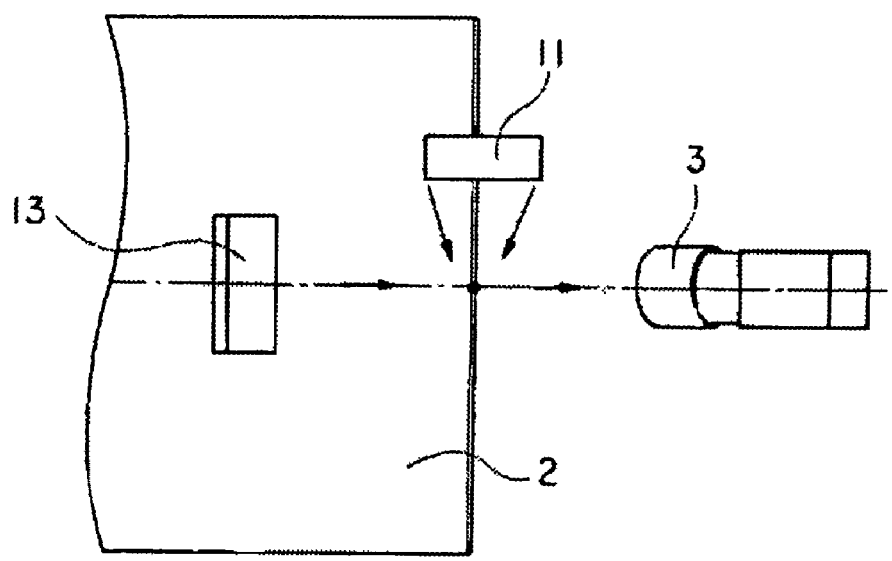
FIG. 3 is a schematic plan view showing an arrangement of an illuminating means and an image pick-up means, in which a single ring illumination is arranged.

As seen from FIG. 3, the C-shaped ring illumination 11 is arranged at only one point on the end face 2a of the glass sheet 2. Further, on the center axis of the ring illumination 11, the illuminating light from the ring illumination 11 is applied to the position slightly deviated from the ring illumination 11, and the end face illuminated with the illuminating light is image-picked up by the CCD cameras 3. However, as seen from FIG. 2, at two positions in the vicinity of the right and left sides of the area to be defect-inspected of the end face 2a of the glass sheet 2, the end face 2a may be inserted in two ring illuminations 11, 11 so that the illuminated positions by these ring illuminations nearly agree with each other, and image-picked up by the CCD cameras 3. Such an arrangement eliminates changes in the intensity of illumination on the end face 2a of the glass sheet 2 and so is more preferable. In this case, the interval between the two ring illuminations is preferably about 60 to 90 mm from the standpoint of assuring the viewing angle of the camera.

In this way, the rounded end face 2a of the glass sheet 2 is loosely inserted in the opening slit 12 of the C-shaped ring illumination 11 so that the end face 2a and the center axis of the ring illumination 11 nearly agree with each other in their positions. For this reason, even if the sectional shape of the end face 2a is an arc-shape, the end face 2a is uniformly illuminated with the illuminating light (see FIGS. 1 to 6).

In this state, the upper and lower planes of the glass sheet 2 placed horizontally as described above are orthogonal to the circular virtual plane of the ring illumination 11, i.e. the plane formed by the external shape of the ring illumination 11 on its LED illumination attaching side. Further, the tangential line of the end face of the glass sheet 2 is also orthogonal to the circular virtual plane of the ring illumination 11.

By an illuminating system of the above ring illumination 11, as regards the defect generated owing to polishing on the arc-shaped plane of the end face 2a of the glass sheet 2, the illuminating light is applied nearly uniformly and sufficiently, thereby permitting the defect such as the scratch, chip, omission of polishing, non-polishing or stain to be detected. However, as regards the chip or "shell" (shell-shaped chip) generated at the ridge which is the boundary 2b between the end face 2a sectionally arc-shaped by grinding or polishing of the upper or lower surface of the glass sheet 2, the illuminating light is not applied sufficiently, thereby giving rise to omission of detection.

In order to surely detect the defects at the ridges 2b, as seen from FIGS. 1 and 2, in addition to the above ring illumination (s), diffusive/permeable illuminations 13, 13 are arranged at the upper and lower positions of the glass sheet 2 and in two upper and lower diagonal positions when seen from the end position of the glass sheet 2 so that the optical axes of the diffusive/permeable illuminations 13, 13 are situated at angles slightly deviated from the optical axes of the CCD cameras 3. Thus, the light source from the diffusive/permeable is applied to the boundaries between the arc-shaped end face of the glass sheet and both upper and lower surfaces thereof.

As seen from FIGS. 1 to 3, the diffusive/permeable illuminations 13 are set so that the illuminating light therefrom enters in a diagonal direction apart from both the front and back surfaces of the glass sheet 2 and is applied to the arc-shaped end face 2a of the glass sheet 2 and the boundaries (ridges) 2b between the end face 2a and glass surfaces, and their light emitting plane of each the diffusive/permeable illuminations 13 occupies the area of about ⅕ to ¼ within the visual field of the camera 3 arranged on the opposite side with respect to the glass sheet 2.

The reasons thereof are as follows. Namely, if the light emitting plane of the diffusive/permeable illumination 13 occupies the area larger than ¼ of the visual field of the camera 3, the "shell" or chip assimilates the diffusive/permeable illuminating light so that they are not discriminated from each other. In addition, where the defect is detected while the glass sheet is carried, the glass sheet may be carried slightly meandering.

On the other hand, if the light emitting plane of the diffusive/permeable illumination 13 occupies the area smaller ⅕ of the visual field of the camera 3, the "shell" or chip at the ridge 2b does not shine, thereby making it impossible to detect the defect.

A detailed explanation will be given of the case where the glass sheet 2 takes a horizontal posture. For example, the illuminating light from the diffusive/permeable illumination 13 located above the glass sheet 2 is mainly applied to the end face 2a of the glass sheet 2 and the boundary between the end face 2a and the lower surface 2c of the glass sheet 2. The illuminating light from the diffusive/permeable illumination 13 located below the glass sheet 2 is mainly applied to the end face 2a of the glass sheet 2 and the boundary between the end face 2a and the upper surface of the glass sheet 2.

The diffusive/permeable illumination 13 may be a plurality of LED elements (light emitting diode elements) arranged two-dimensionally in a matrix shape. The width of the diffusive/permeable illumination 13 facing the camera side, i.e. its side in parallel to the end face is preferably twice or more than the visual field of the camera. Its height may be designed so that the light emitting plane of the diffusive/permeable illumination 13 occupies the area of about ⅕ to ¼ within the visual field of the camera 3 arranged on the opposite side with respect to the glass sheet.

Incidentally, the C-shaped ring illumination 11 may have the shape of a semi-circle or larger giving the light source over an angle of 180 or more degrees. Preferably, it extends over a wide range so that remaining portion exclusive of the slit portion 12 in which the end of the glass sheet 2 can be loosely inserted constitutes the light source.

Further, the ring illumination 11 may be a high frequency fluorescent lamp formed in a C-shape. However, in view of easiness of manufacture, life, breakage, etc, as seen from FIGS. 5 and 6, the ring illumination 11 is preferably a C-shape illumination in which a large number of LED elements 11a, 11a, . . . are preferably arranged concentrically in plural arrows so that the light emitted from each of the LED elements 11a, 11a . . . is applied to nearly the same area on the center axis of the ring illumination 11. In this case, the shape constituted by the optical axes of the large number of LED elements 11a, 11a is conical.

The angle of attaching the LED elements of the ring illumination 11 is preferably 10 to 45 degrees from a horizontal direction in view of a desired interval of 60 to 90 mm between the two ring illuminations 11, 11 when they are oppositely arranged.

As shown in FIGS. 1 to 3, by means of two illuminating systems which include the illumination system of the ring illumination(s) 11 arranged at the end face 2a of the glass sheet 2 and the illuminating system of the diffusive/permeable illuminations 13 in the upper and lower diagonal directions to the glass surfaces 2c, the illuminated round end face 2a of the glass sheet 2 and the areas in the vicinity of the boundaries thereof for the upper and lower surfaces 2c are simultaneously image-picked-up by at least two CCD cameras 3, 3. The images thus obtained are processed by the image processing device 4 (see FIG. 9) thereby to determine the presence/absence of the defects.

The camera 3 located on the upper diagonal side of the glass sheet 2 is to image-pick up both areas of the rounded end face 2a ground at the end of the glass sheet 2 and the area in the vicinity of the boundary between the end face 2a and the upper surface of the glass sheet 2. Using this camera 3, it is difficult to image-pick up the area in the vicinity of the boundary between the end face 2a and the lower surface of the glass sheet 2 because the visual field of this camera is blocked by the ground area of the rounded end face 2a.

Likewise, the camera 3 located on the lower diagonal side of the glass sheet 2 is to pick up both areas of the rounded end face 2a ground at the end of the glass sheet 2 and the area in the vicinity of the boundary between the end face 2a and the lower surface of the glass sheet 2. Using this camera 3, it is difficult to pick up the area in the vicinity of the boundary between the end face 2a and the lower surface of the glass sheet 2 because the visual field of this camera is blocked by the ground area of the rounded end face 2a.

The image picked up by the CCD camera 3 will be processed in the following manner.

Figure 10:
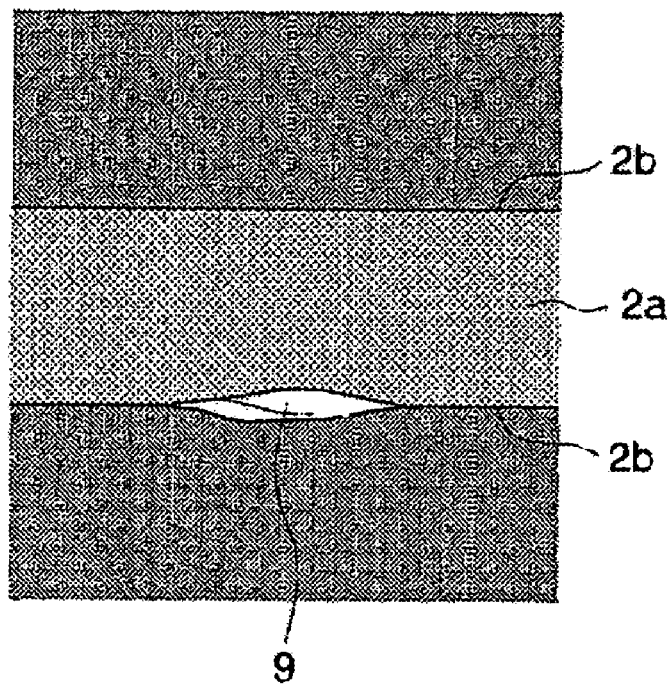
FIG. 10 is an original image of a chip defect picked up by a CCD camera.
Figure 12:
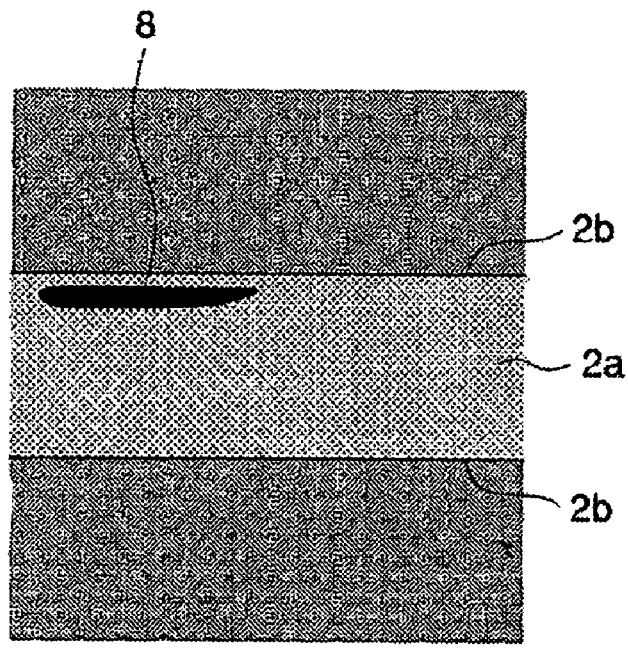
FIG. 12 is an original image of "omission of polishing" picked up by a CCD camera.

The end face 2a rounded by grinding or polishing at the end of the glass sheet 2a is an aggregation of fine scratches due to abrasive, and appears a ground glass. The image picked up by the camera 3 is shown in a grayish color. As regards the original image of the end face 2a picked up by the CCD camera 3, assuming that the darkest gray level in e.g. a 256-level gray scale is 0 and the brightest gray level is 255, the defect of "scratch", "shell", "chip" or "stain" provides a "bright" signal higher than level A whose gray level is on the bright side and so is shown whitish as shown in FIG. 10. The defect of "non-polishing" or "omission of polishing" is shown blackish because it provides a "dark" signal higher than level B whose gray level is on the dark side as shown in FIG. 12.

Figure 11:
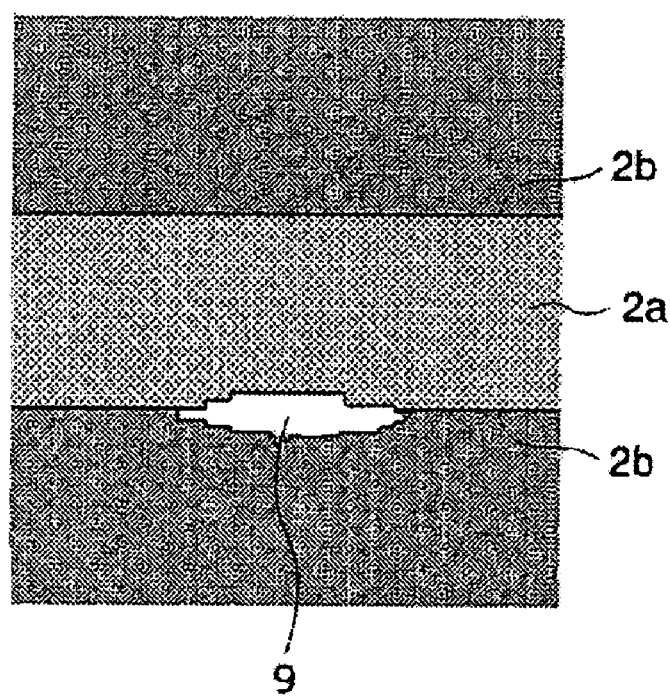
FIG. 11 is an image binary-digitized with an upper limit level of a "bright" signal side of the chip defect picked up by a CCD camera.

Thus, the original image picked up (see FIG. 10) is binary-digitized in terms of the upper limit level of a gray scale. Assuming that the defective area is "bright" and the normal area is "dark", the binary-digitized image thus obtained (FIG. 11) is subjected to "labeling". Thus, according to the position or size of the pixel which is bright in the defective area, the kinds of the surface defect of "scratch" or "stain" and the edge defect of "shell" or "chip" are determined.

Namely, the kinds of the defects can be specified on the basis of the position of the "bright" signal and the distance of the end processed region from the edge. For example, if the defect is contained in the end processed region, it is regarded as the surface defect 8 of "scratch" or "stain". If the defect straddles the edge of the end processed region, or is located outside the edge, it is regarded as the edge defect 9 of "shell" or "chip".

Figure 13:
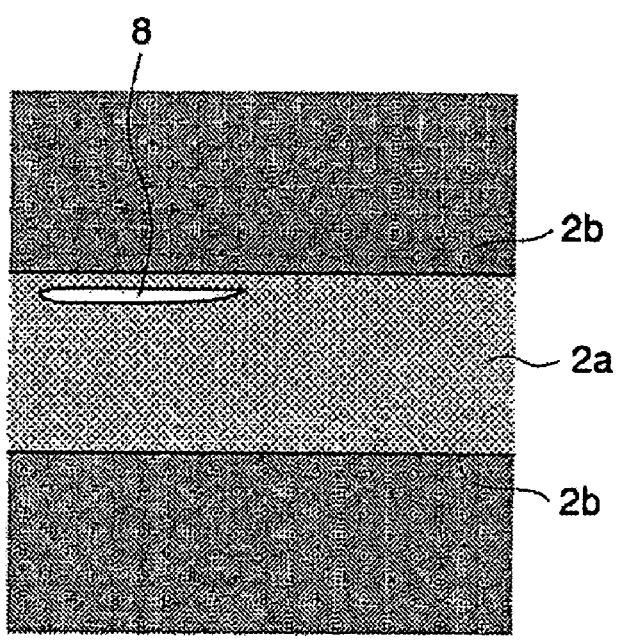
FIG. 13 is an image binary-digitized with a lower limit level of a "dark" signal side of the "omission of polishing" defect picked up by a CCD camera.

Likewise, the original image picked up (see FIG. 12) is binary-digitized in terms of the lower limit level of the gray scale and inverted. Assuming that the defective area not higher than the lower limit level is "bright" and the normal area is "dark", the binary-digitized image thus obtained (FIG. 13) is subjected to "labeling". Thus, according to the position or size of the pixel which is bright in the defective area, the defect of "non-polishing" and "omission of polishing" is determined, thereby determining the presence/absence and kind of the defect.

The above upper and lower limit levels are empirically set according to the kind of the glass sheet 2, and these settings can be changed as required.

Further, in addition to setting the standard for determining the surface defect 8 and the edge defect 9, another standard is set for checking the image quality such as the coarseness of the polished face of the glass sheet for the visual field of the image of the end face of the glass sheet picked up by each CCD camera. In this case, the accumulated value of the brightness within the visual field is divided by the number of pixels (area value) within the visual field thereby to acquire the average density. This average density is compared with a reference value set previously. If this average density is not smaller than the reference value, it is determined that the pertinent image quality is defective.

In this case, if the polished face is coarse and shown whitish, the image quality is poor and so assumed as being defective. If the polished face is fine and shown blackish, the image quality is within the reference value and so assumed as being good.

As described above, at least two CCD cameras 3 are prepared. In this case, the original image picked up by each CCD camera 3 is fetched into the image processing device 4. The original image thus fetched is binary-digitized separately at two limit levels of the lower limit level of the "dark" side and the upper limit level of the "bright" side, thereby determining the presence/absence of the defect.

The pixel whose gray level is between the lower limit level and upper limit level is recognized to be within the normal range. However, even if the gray level exceeds the upper limit level, according to the position or size, as the case may be, the pixel (s) may be regarded as being within the normal range. In this case, the image quality may be determined on the basis of the upper limit level, lower limit level and other determining standard, which are previously set according to the products.

The above CCD camera 3 is a two-dimensional camera, but may be a line camera. In this case, as required, the image data scanned by the line camera may be stored in the microprocessing device 5 (see FIG. 9) so that they are processed in an area assembled two-dimensionally.

The above glass sheet 2 is directed to the general glass sheet with the end edge being chamfered or the end face being polished. However, the glass sheet 2 is effective for various square display substrates of the flat display panel for e.g. the liquid crystal display, plasma display, field emission display or organic EL display. Further, the glass sheet 2 may be a glass sheet having a different shape such as a window glass sheet for a vehicle.

Figure 8:
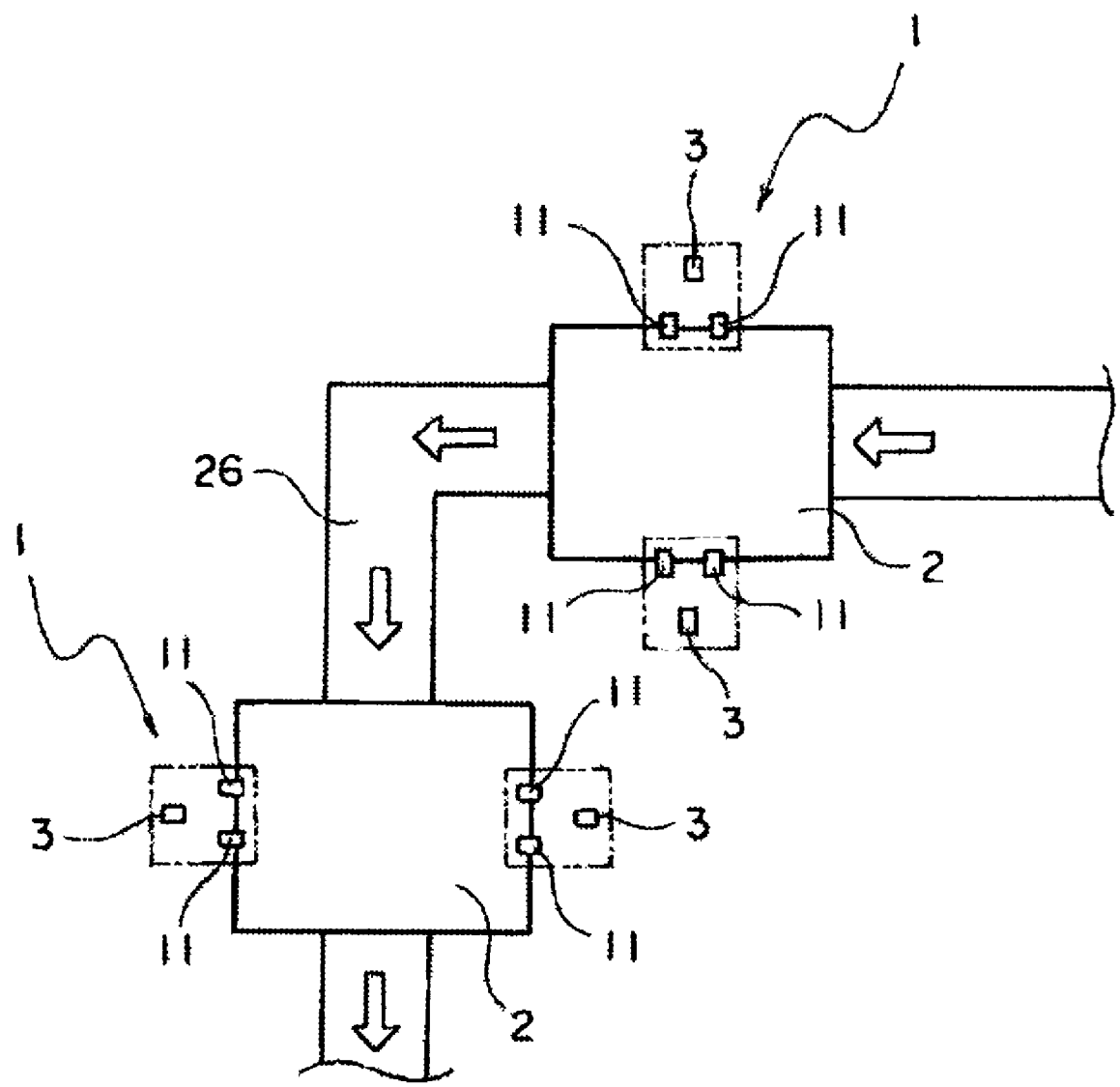
FIG. 8 is an entire view for explaining the outline the defect detecting device according to a first embodiment.

Additionally, the defect inspection on the entire periphery, of the end face 2a of the glass sheet 2 can be made by the following method, as shown in FIG. 8. Defect detecting devices 1, each including at least, the ring illuminations 11 and at least two CCD cameras 3, 3, are fixedly arranged at the positions of the two sides in parallel to the carrying direction of the glass sheet 2 to be carried so that they sandwich the glass sheet 2. The end faces 2a on the two sides of the glass sheet 2 are successively inspected when the glass sheet 2 passes the defect detecting devices 1. The carrying direction of the glass sheet 2 is 90-degrees converted so that the non-inspected two sides of the glass sheet 2 are in parallel to the carrying direction. The defect detecting devices 1, each including the illuminating system and cameras 3 as described above are arranged at the positions on the two sides non-inspected. The end faces 2a on the two sides of the glass sheet 2 are successively inspected when the glass sheet 2 passes the defect detecting devices 1.

The following method can be also adopted. The illuminating device 10 equipped with at least the ring illumination 11 and the image pick-up which is the CCD camera 3 are attached to the hand (not shown) of a multi-joint robot (not shown). The hand is moved sequentially along the end face of the outer periphery of the glass sheet 2 so that the entire periphery of the end face of the glass sheet 2 is sequentially image-picked up. The image signals thus obtained are processed by the image processing device 4 to determine the defects on the end face 2a. Incidentally, if there is a means capable of moving the illuminating device and image pick-up device, they may be attached to an ordinary robot (for example, linear motion system).

Further, the following method can also be adopted. While the glass sheet is carried, the end faces of the two sides in parallel to the carrying direction are inspected by the first defect detecting device. While the glass sheet stops, the end faces of the remaining two sides orthogonal to the above two sides are inspected by the second defect detecting device.

Where the defect detection is done while the glass sheet is carried, the glass sheet is preferably carried in its horizontal posture on a carrying line. However, the defect detection can be done while the glass sheet is carried in its slanting posture on a slanting conveyer.

Figure 4:
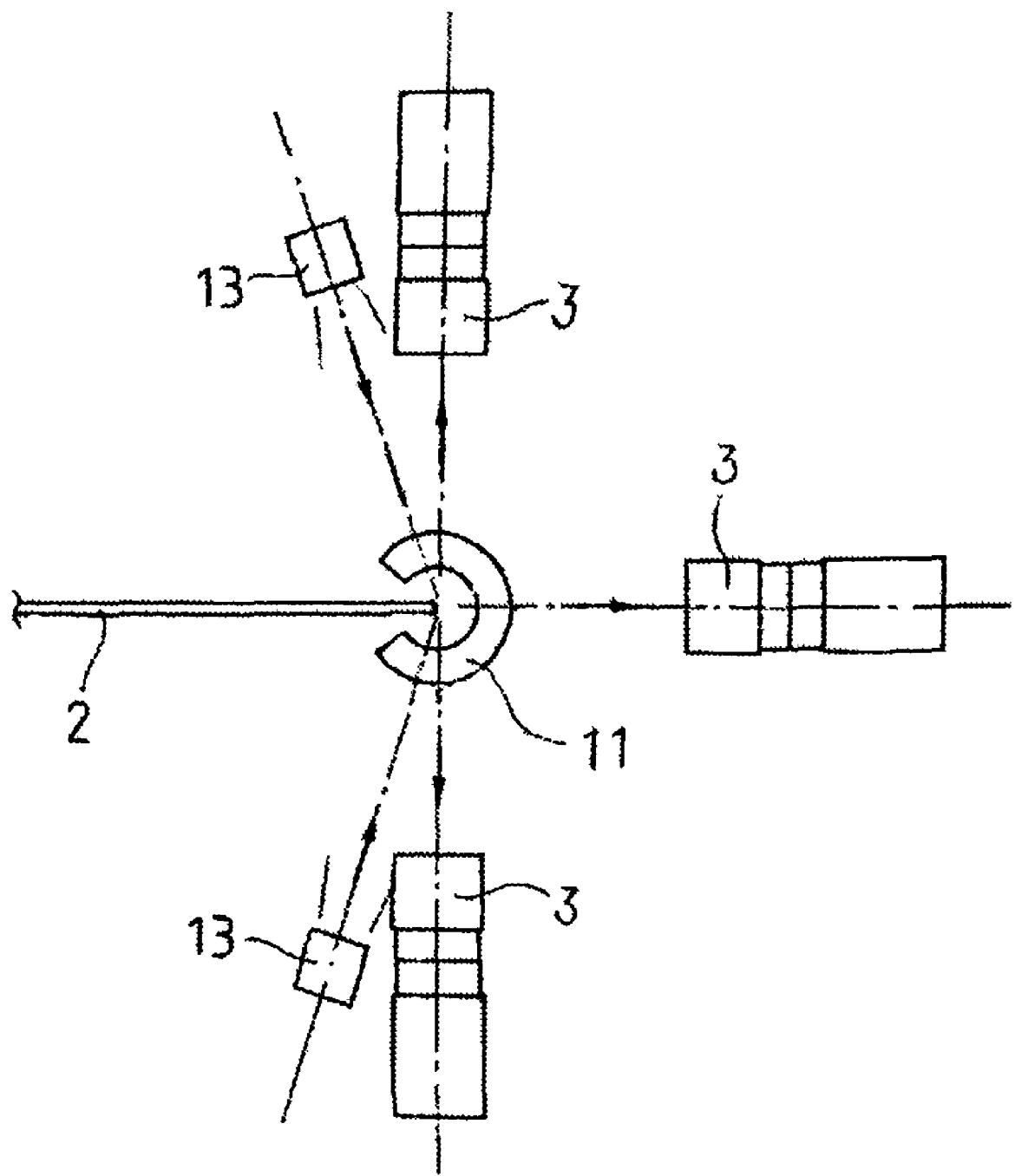
FIG. 4 is a schematic side view showing an arrangement of an image pick-up means in which three CCD cameras are arranged.

Incidentally, in the above detailed explanation, the vertical position and vertical direction of the glass sheet in the case where the glass sheet is carried in its horizontal posture should be interpreted as the front-back position and front-back direction or the front-rear position and front-rear direction in the case where the glass sheet is carried in its slanting posture.

Where three CCD cameras 3 are arranged as the image pick-up devices, assuming that the glass sheet is horizontally placed as shown in FIG. 4, the one CCD camera 3 may be arranged in a horizontal direction at an angle of 0 degree when the glass sheet plane is externally extended and in the direction perpendicular to the side to be inspected of the glass sheet 2 in order to image-pick up the area to be inspected of the end face; and the other two cameras may be arranged in the direction just above and just below the end of the glass sheet plane.

In this case, the CCD camera 3 arranged in the horizontal direction may inspect the defect on the arc-shaped end face of the glass sheet and the two CCD cameras 3, 3 arranged in the vertical direction may inspect the defect in the vicinity of the boundary 2b between the end face 2a and the glass sheet plane, respectively.

The operation of the invention will be explained below.

Figure 6:
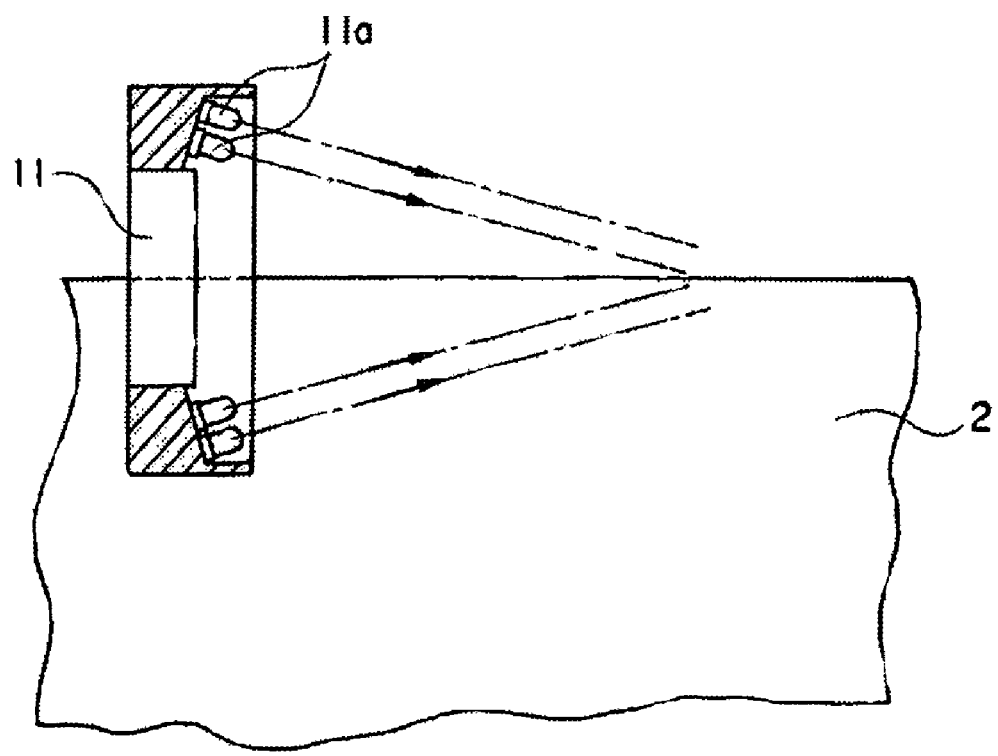
FIG. 6 is a longitudinal sectional view of a ring illumination.

As seen from FIGS. 5 and 6, the ring illumination 11 is partially notched like a slit to form the C-shape-shape ring illumination 11 and the end face 2a of the glass sheet 2 in loosely inserted in the slit-like portion 12. For this reason, the illuminating light from each of the LED elements 11a arranged in an arc shape is uniformly applied to each of segments of the end face nearly arc-shaped in section under comparatively the same condition.

Specifically, as seen from FIG. 6, the ring illumination 11 is designed so that the illuminating light beams from the LED elements 11a are applied concentrically toward the direction slightly deviated from the center axis of the ring illumination 11 so that they form a conical shape. Therefore, the end face 2a illuminated by the ring illumination 11a does not generate uneven illumination. Thus, the end face 2a can be image-picked up by the CCD camera 3 under a good illuminating condition so that the inspection with less omission of detection of the defect can be performed.

Incidentally, the illuminating light from the ring illumination 11 is preferably applied to the position slightly deviated from the center of the ring illumination 11 on the center axis of the ring illumination 11, but may be applied to position corresponding to the center of the ring illumination 11. In this case, the camera may be away from the ring illumination to image pick up the end face in a diagonal direction so that the end face is seen from oblique beside.

Further, the position to be illuminated by the illumination must agree with the visual field to be picked up by the CCD camera 3. In addition, this position is at the end face 2a on which the section at the end of the glass sheet 2 is arc-shaped. Thus, the arc-shaped end face 2a of the glass sheet 2 can be uniformly illuminated by the ring illumination 11.

Additionally, as seen from FIGS. 2 and 3, if the light source is applied to the position of the end face 2a slightly deviated from the center of the ring illumination 11, the camera 3 can be arranged to take an image in the direction perpendicular to the tangential direction of the end face 2a of the glass sheet 2a to image pick up the end face 2a. This manner gives high detection accuracy and so is preferable.

Where the light source is applied to the end face 2a position corresponding to the nearly central position of the ring illumination 11, the end face 2a of the glass sheet 2 is obstructed by the attaching member for the ring illumination 11. Therefore, the camera 3 cannot be arranged in the direction perpendicular to the tangential direction of the end face 2a. So, the camera must be away from the ring illumination 11 to image pick up the end face in a diagonal direction so that the end face is seen from oblique beside. This attenuates the detection accuracy and so is not preferable.

Also where the ring illumination 11 is located at a single point for the end face 2a of the glass sheet 2 as shown in FIG. 3, the defect on the end face 2a can be sufficiently detected. However, as seen from FIG. 2, the ring illumination is preferably located at two points. In this case, as seen from FIG. 2, the end face 2a of the glass sheet 2 is loosely inserted in the two ring illuminations 11 in the vicinity of the right and left sides of the area to be inspected of the glass sheet 2. The illuminating light is applied so that the position illuminated by the ring illuminations nearly agrees with the area to be defect-inspected and image-picked up by the CCD cameras 3. This arrangement eliminates the unevenness of illuminating intensity for the end of the glass sheet 2 and so is more preferable.

Further, in the defect detecting device 1 according to the invention, as seen from FIGS. 1 to 3, the CCD cameras 3 are arranged in the direction perpendicular to the end face edge of the glass sheet 2 illuminated by the ring illumination(s) 11 formed at least in a C-shape, and further the boundary between the end face edge and the glass sheet plane 2c is illuminated by the permeable illuminating light and picked up by the camera 3. If the image picked up contains no defect, the light is dispersed because the polished area is opaque. Thus, the quantity of light incident on the camera 3 is decreased and the image is gray. On the other hand, if the image picked up contains any defect such as "chip", the polished area shines bright owing to the lens effect and so is taken as a bright signal. Accordingly, it can be determined whether or not the above boundary is good.

Embodiment 1

The glass sheet 2 to be inspected is a glass sheet having a small to large size, for example, a square glass sheet with sides each having a length of 300 mm to 2000 mm. The end face 2a of the glass sheet 2 is processed in a rounded arc shape in section.

Figure 7:
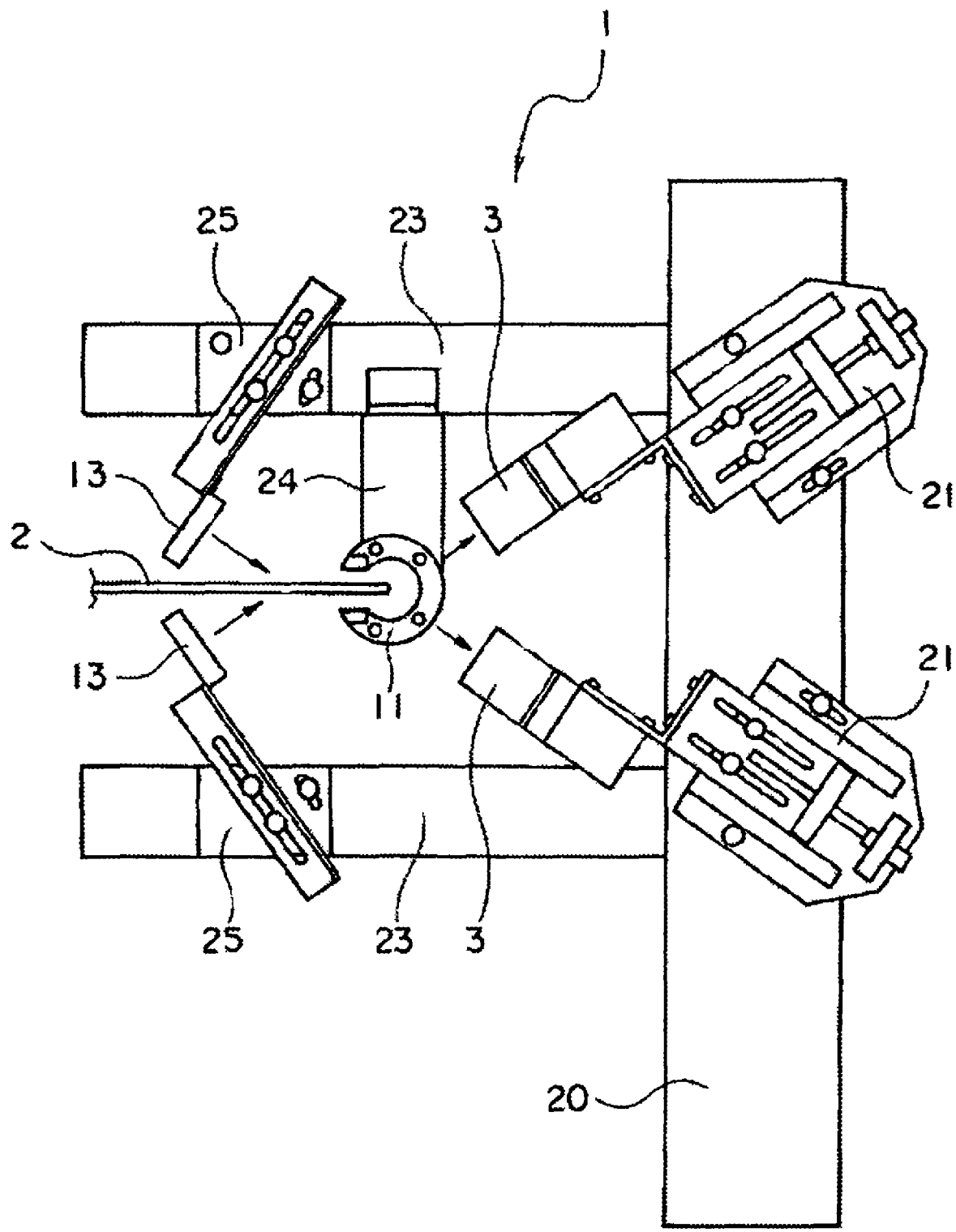
FIG. 7 is a front view of a defect detecting device according to the first embodiment.

As seen from FIG. 8, on both sides of the carrying line 26 for the glass sheet, the defect detecting devices 1 as shown in FIG. 7 are arranged. As the camera 3 which is the image pick-up device, two two-dimensional CCD area cameras are employed. The viewing angle of each camera 3 is about 20 mm×20 mm to 50 mm×50 mm. The angle of attaching the cameras 3 is 30 to 45 degree in both upper and lower directions from a horizontal plane. The cameras 3 are attached to a vertical frame 20 by means of attaching members 21 so that the edge of the glass sheet is located at the center of the visual field. The adjusting angle is freely adjustable.

As seen from FIG. 2, the ring illumination 11 serving the illuminating device 10 can be prepared by processing a part of a ring illumination 11 commercially available in a slit to provide the C-shape. A plurality of LED elements 11a, 11a are concentrically arranged in two or three columns at regular pitches. The illuminating direction of each LED element is inclined at e.g. 15 degrees from the center axis of the illumination 11 and the optical axes of the LED elements 11a, 11a, ... constitute a conical shape. The interval between the two ring illuminations 11, 11 is set at e.g. 80 mm.

Further, as seen from FIG. 7, two horizontal frames 23, 23 perpendicular to the above vertical frame 20 and extended horizontally are fixed at the two positions above and below the glass sheet 2, and the ring illumination 11 is attached to the upper horizontal frame 23 through an attaching member 24.

The nearly C-shaped ring illumination(s) 11 having a slit-like notch is arranged so that the illuminating light therefrom is uniformly applied to the rounded end face 2a at the end of the glass sheet 2. The end face 2a of the glass sheet 2 is loosely inserted in the slit-like portion 12 of the ring illumination 11 so that the end face 2a is located on the center axis of the ring illumination 11.

As seen from FIG. 8, while the glass sheet 2 is carried by the carrying line 26, its end face 2a passes the ring illuminations so that it is loosely inserted in the opening slit 12 of each the ring illuminations 11 arranged on both sides of the carrying line 26. When the end face is loosely inserted, the end of the glass sheet 2 illuminated by each the LEDs 11a, 11a, ... of the ring illuminations 11 is image-picked up by the CCD cameras 3. The image is processed for each of the cameras, and defect detection is done on the basis of levels in the gray scale.

The diffusive/permeable illuminations 13 are set at an angle from the horizontal plane in both upper and lower directions of the glass sheet 2 so that their illuminating light is applied to the arc-shaped end face of the glass sheet and boundary between the end face and the glass sheet plane and the light-emitting plane of the diffusive/permeable illumination 13 occupies about ⅕ to ¼ of the visual field of the camera 3.

Incidentally, as seen from FIG. 7, the diffusive/permeable illuminations 13, 13 are attached to the horizontal frames 23, 23 provided above and below the end of the glass sheet 2 through attaching members 25, 25, respectively.

In order to prevent uneven illumination, the diffusive/permeable illumination 13 has also a milky-white diffusing plate attached on the LED elements arranged two-dimensionally in a matrix shape. The illumination may be done using a fluorescent lamp in place of the LED element.

The glass sheet 2 is carried at e.g. a constant speed on the carrying line 26. The end of the glass sheet 2 is image-picked up by the CCD camera 3 so that it is sectioned at the pitch unit corresponding to the visual field width of the camera, and the defect inspection is done for each of the images picked up.

Since the area camera 3 is employed in this embodiment, the visual field for image pick-up corresponds to the pitch width which is the sectioned area. However, the region to be picked up by the camera 3 is set at an area slightly larger than the pitch width and the vicinities of the boundary between the images acquired are superposed to prevent omission of inspection, thereby continuously inspecting the end face.

A specific explanation will be given of the flow of the inspection of the glass sheet 2.

First, as shown in FIG. 8, the square glass sheet 2 is carried by the carrying line 26. When the glass sheet 2 approaches the defect detecting device 1, the ring illumination 11 and the diffusive/permeable illumination 13 of the illumination device 10 are turned on by a control unit not shown. The glass sheet 2 is carried in the visual field for image pick-up by the CCD camera 3. Thus, when the tip corner of the end face 2a of the glass sheet 2 is detected, assuming that the corner is a starting position of an inspected area of the end face 2a, the images are fetched into the image processing device 4 from the position slightly displaced from the corner.

Figure 9:
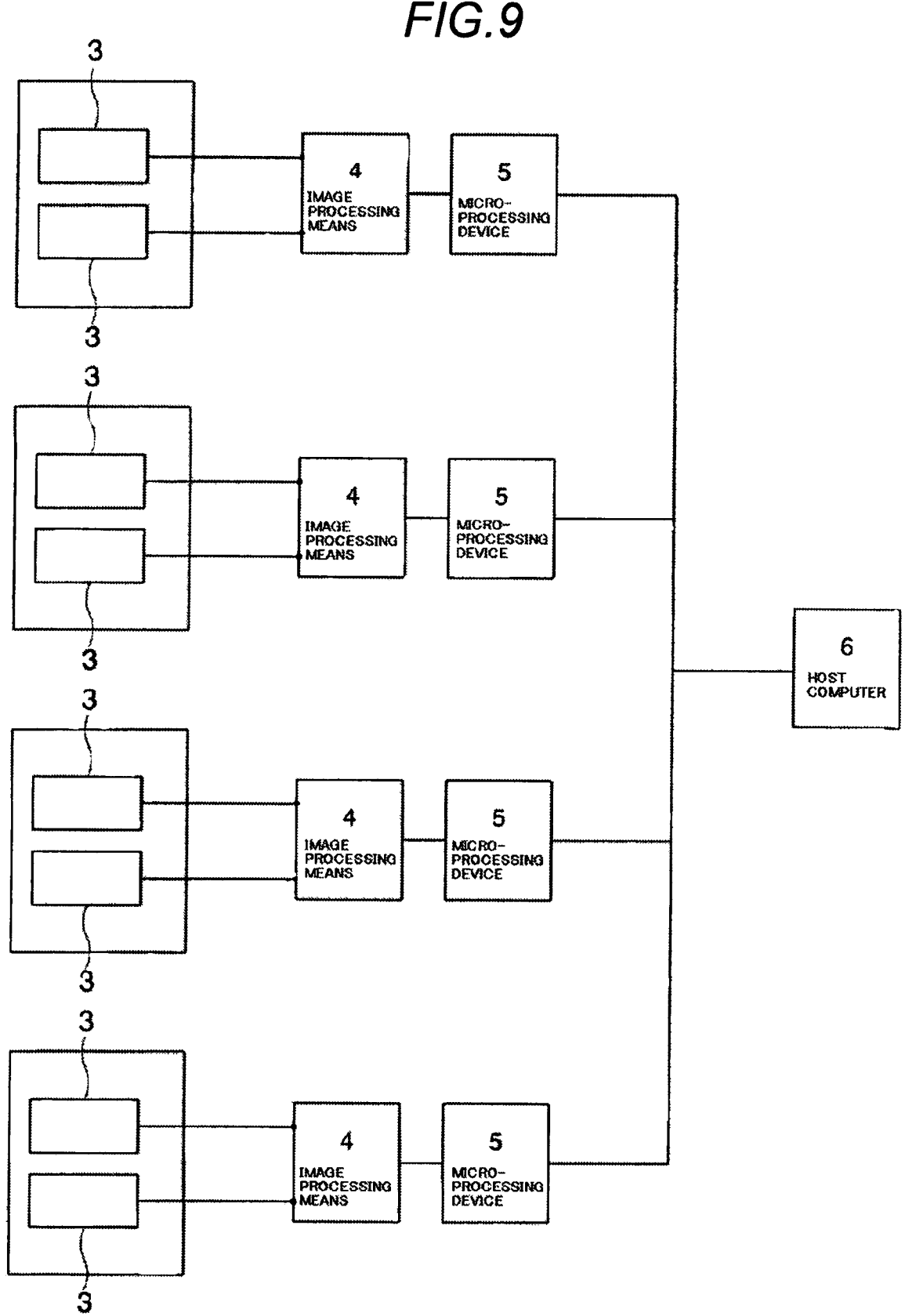
FIG. 9 is a schematic view showing the entire configuration of the defect detecting device according to the invention.

As seen from FIG. 9, as regards the image fetched into the image processing device 4 from the CCD camera 3, on the basis of the sheet thickness information of the glass sheet 2 previously set and registered and the one edge 2b picked up by the one camera 3, the other edge 2b is computed thereby to determine the area to be computed. The picked-up original image having 256 levels in the gray scale which is the area to be computed is binary-digitized in terms of the upper limit level on the "bright" side of the previously set, i.e. the upper limit level in the gray scale. The binary-digitized image thus obtained is subjected to "labeling". On the basis of the distance between the position of the "bright" signal shown and the edge 2b of the processed end face 2a, the kinds of the defect is determined.

For example, if the defect is contained in the processed end face 2a, it is regarded as the surface defect 8 of "scratch" or "stain". If the defect straddles the edge 2b of the processed end face 2a or is located outside the edge 2b, it is regarded as the edge defect 9 of "shell" or "chip". This information is stored in a micro-processing device (computer) 5.

Likewise, the original image picked up is binary-digitized in terms of the lower limit level previously set, e.g. the lower limit level of the gray scale and thereafter inverted. Assuming that the defective area not higher than the lower limit level is "bright" and the normal area is "dark", the binary-digitized image thus obtained is subjected to "labeling". Thus, according to the position or size of the pixel which is bright in the defective area, the defect of "non-polishing" and "omission of polishing" is determined, thereby determining the presence/absence and kind of the defect.

The same processing as described above is also executed for another camera 3.

Incidentally, the glass sheet 2 is carried at a constant speed on the carrying line 26. The end of the glass sheet 2 is image-picked up and inspected by the CCD camera 3 so that it is sectioned at the pitch unit corresponding to the visual field width of the camera. In this case, with the vicinities of the boundary between the front end and rear end of each image being slightly superposed, the inspection is continued until the corner of the end face at the rear end is detected.

Upon completion of the inspection of the two sides of the glass sheet 2, the carrying direction is inverted so that the non-inspected two sides of the glass sheet 2 are in parallel to the carrying direction. The defect detecting devices 1 each consisting of the illuminating system and camera 3 as described above are arranged at the positions corresponding to the non-inspected two sides, respectively. While the glass sheet 2 passes the defect detecting devices 1, the end faces 2a of the two sides of the glass sheet 2 may be successively inspected.

In this way, if the defect detection is executed for the four sides of the glass sheet and the data thus acquired are stored in the host computer, the management can be facilitated.

Embodiment 2

Embodiment 2 is different from the Embodiment 1 in that with the glass sheet being fixed, the inspecting device including the illuminating device and image pick-up device is driven over the entire periphery of the glass sheet to inspect the defect on the end face of the outer periphery the glass sheet 2.

The arrangement condition of the direction/angle of the illuminating device 10 and image pick-up device for the glass sheet 2 is set at the same condition as in the first embodiment. The processing device for the images acquired and others are entirely the same as the Embodiment 1.

As for the apparatus to be driven over the entire periphery of the glass sheet, with the illuminating device and image pick-up device being attached to the hand (not shown) of the multi-joint robot (not shown), this hand is sequentially moved along the end face of the outer periphery the glass sheet 2. Thus, the end face of the glass sheet is image-picked up and the image signal thus acquired is identified by the image processing device thereby to inspect the presence/absence of the defect.

Incidentally, where inspection is to be done on the way of the carrying line, the glass sheet must be once stopped to assure the space over the entire periphery of the glass sheet so that the inspecting apparatus including the illuminating device and the image pick-up device can be moved. To this end, the mechanism for lifting these device supported in the vicinity of its center of the glass sheet may be provided.

Embodiment 3

Figure 14:
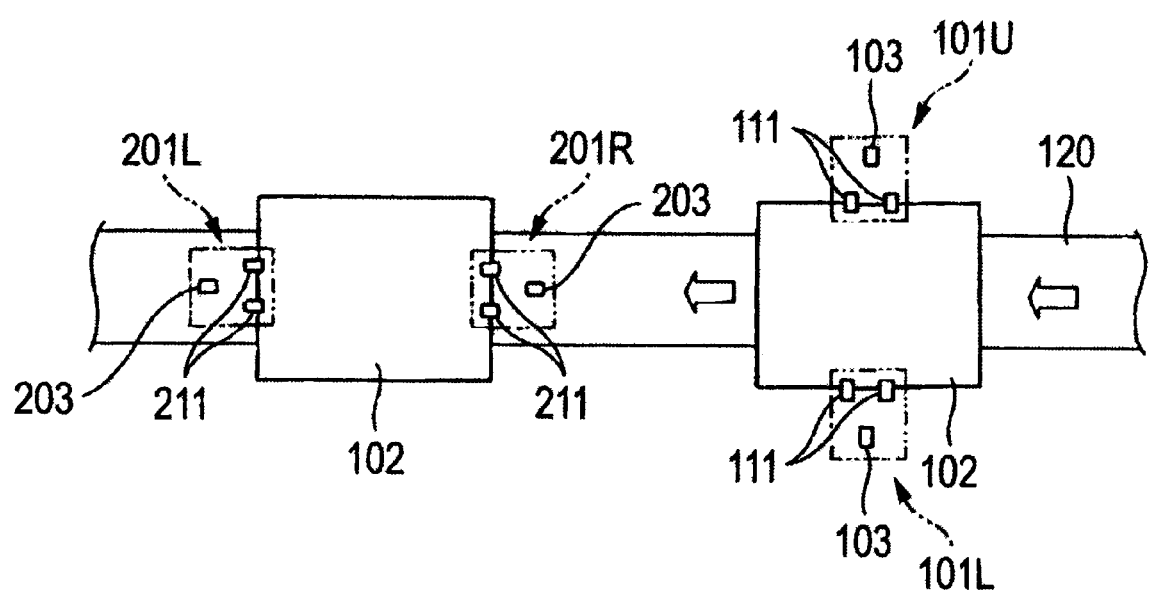
FIG. 14 is a side view of a defect detecting device according to the third embodiment.

FIG. 14 shows the defect detecting device for the end face of the glass sheet according to Embodiment 3. The defect detecting device includes first inspecting detecting devices 101U, 101L for inspecting the first and third sides of the glass sheet 102 which is moving, and movable second defect inspecting devices 201R, 201L for inspecting the second and fourth sides of the glass sheet 102 which stops. Incidentally, the glass sheet 102 is rectangular so that the first and third sides are in parallel to each other, the second and fourth sides are in parallel to each other, and the first and third sides are perpendicular to the second and fourth sides.

The glass sheet 102 is carried on the carrying device 120. The carrying device 120 may be a system which carries the glass sheet 102 in its slanting posture or a system which carries the glass sheet 102 in its horizontal posture. On both sides of the carrying path of the carrying device 120, the first defect inspecting devices 101U and 101L are provided for inspecting the two sides (first and third sides) in parallel to the carrying direction of the glass sheet 102. Where the glass sheet 102 is carried in its slanting posture, the first defect inspecting devices are an upper defect inspecting device 101U which inspects the upper side corresponding to the first side and a lower defect inspecting device 101L which inspects the lower side corresponding to the third side. The first defect inspecting devices 101U, 101L are provided with the illuminating device 111 and image-pickup device 103, respectively. When the glass sheet 102 passes the positions corresponding to the first defect inspecting devices 101U, 101L, the first defect inspecting devices 101U, 101L inspect the end face of each the two sides in parallel to the carrying direction of the glass sheet 102.

The glass sheet 102 carried by the carrying device 120 stops at the positions corresponding to the second defect inspecting devices 201R, 201L. The second and fourth sides of the glass sheet 102 stopped are inspected by the second defect inspecting devices 201R, 201L. The second defect inspecting devices 201U, 201L are provided with the illuminating device 211 and image-pickup device 203, respectively. The second defect inspecting devices 201R, 201L are attached to the arm (not shown) of the robot (not shown) and movable in parallel to the second and fourth sides of the glass sheet 102. The second defect inspecting devices 201R, 201L are moved along the second and fourth sides of the glass sheet 102 thereby to inspect the end face of each the second and fourth sides. Incidentally, where the glass sheet 102 carried in its slanting posture stops in its slanting posture, the second side and fourth sides correspond to the right side and left side, respectively and the second defect inspecting devices 201R, 201L moves vertically in the slanting direction. Upon completion of carrying, the glass sheet 102 may be moved from the carrying device 120 to the inspecting device provided with the second defect inspecting devices 201R, 201L.

Incidentally, in the Embodiment 3, the illuminating device 111, 211 and the image pick-up device 103, 203 are the same as the illuminating device 11 and the image pick-up device 3 in the Embodiment 1 and the Embodiment 2. As in the Embodiment 1 and the Embodiment 2, using the illuminating devices 111, 211 and the image pick-up devices 103, 203, the defects on the end face of the glass sheet are detected.

The invention has been explained in detail and referring to the specific embodiments. However, it is apparent to those skilled in the art that the invention can be changed or modified in various manners without departing from the spirit and scope of the invention.

This application is based on Japanese Patent Application (Patent Application No. 2005-034238) filed on Feb. 10, 2005 and the contents thereof are incorporated herein by reference.

INDUSTRIAL APPLICABILITY

The defect detecting device and defect detecting method according to one or more embodiments of the invention are employed to detect the defects on the end face of a glass sheet having an arc-shaped end face ground at its end or seaming face.

The invention claimed is:

1. A device for detecting a defect on an end face of a glass sheet, the device comprising:
    an image pick-up device including at least two CCD cameras for image-picking up the end face of the glass sheet from outside the glass sheet and in two directions diagonal to both front and back surfaces of the end face of the glass sheet;
    an illuminating device including a C-shaped ring illumination which is capable of applying illuminating light in its center axis direction and has a slit; and
    an image processing device adapted to process an image signals acquired from the CCD cameras and determine a quality of the end face,
    wherein the glass sheet is loosely inserted in the opening slit so that the end face agrees with a center axis of the ring illumination;
    the illuminating device applies the illuminating light to the end face; and
    the image signals acquired from image pick-up of the end face by the image pick-up device are processed by the image processing device to detect the defect on the end face.

2. The device or detecting a defect on the end face of a glass sheet according to claim 1, wherein the glass sheet has the end face which is chamfered to constitute an arc-shaped end face or a smooth ridge.

3. The device for detecting a defect on the end face of a glass sheet according to claim 1, wherein the illuminating device comprises two C-shaped ring illuminations arranged in vicinities of both right and left sides of an area to be defect-inspected of the end face of the glass sheet; and
    each of the ring illuminations illuminates the area to be defect-inspected.

4. The device for detecting a defect on the end face of a glass sheet according to claim 1, wherein the illuminating device further includes diffusive/permeable light sources adapted to apply illuminating light to the end face of the glass sheet from two directions diagonal to both front and back surfaces of the glass sheet.

5. The device for detecting a defect on the end face of a glass sheet according to claim 3, wherein the illuminating device further comprises diffusive/permeable light sources that apply illuminating light to the end face of the glass sheet from two direction diagonal to both front and back surfaces of the glass sheet.

6. The device for detecting a defect on the end face of a glass sheet according to claim 1, wherein the ring illumination comprises a plurality of LED elements arranged concentrically.

7. The device for detecting a defect on the end face of a glass sheet according to claim 3, wherein the ring illumination comprises a plurality of LED elements arranged concentrically.

8. The device for detecting a defect on the end face of a glass sheet according to claim 1, further comprising:
    a carrying device adapted to carry the glass sheet so that sides of the glass sheet are in parallel to a carrying direction,
    wherein the illuminating device and the image pick-up device are arranged in the vicinity of the end face of each of both sides of the glass sheet.

9. The device for detecting a defect on the end face of a glass sheet according to claim 1, wherein the illuminating device and the image pick-up device are attached to a hand of a robot; and
    the hand is sequentially moved along an end face on an outer periphery of the glass sheet so that the end face of the glass sheet is image-picked up and the acquired image signal is sequentially processed by the image processing device.

10. The device for detecting a defect on the end face of a glass sheet according to claim 1, comprising:
    a first defect inspecting device adapted to inspect an end face of a side in parallel to a carrying direction of the glass sheet being carried, the first defect inspecting device being fixed with respect to a carrying; and
    a second defect inspecting device adapted to inspect an end face of a side perpendicular to the carrying direction of the glass sheet being carried, the second defect inspecting device being movable with respect to the glass sheet,
    wherein the first defect inspecting device and the second inspecting device are respectively provided with illuminating devices and image pick-up devices.

11. A method for detecting a defect on an end face of a glass sheet, the method comprising:
    loosely inserting the end face of the glass sheet into an opening slit of a C-shaped ring illumination;
    applying illuminating light of the ring illumination to an area of the end face to be inspected where a position of the end face and a center axis of the ring illumination overlap;
    image-picking up the end face by two CCD cameras;
    comparing a gray level of an image signal acquired by image-picking up with upper and lower limit levels previously set; and
    detecting a presence/absence and a kind of the defect based on a position, size and shape of a pixel signal higher than the upper limit level or lower than the lower limit level.

12. The method for detecting a defect on the end face of a glass sheet according to claim 11, further comprising:
    carrying the glass sheet by a carrying device so that a side of the glass is in parallel to a carrying direction;
    arranging at least an illuminating device including the C-shaped ring illumination and an image pick-up device for image-picking up the end face illuminated by the illuminating device in a vicinity of the end face of each of both sides of the glass sheet;
    processing the image signal of the end face image-picked up by the image pick-up device by an image processing device; and
    detecting the presence/absence of the defect.

13. The method for detecting a defect on the end face of a glass sheet according to claim 11, comprising:
  attaching, to a hand of a robot, at least an illuminating device including the C-shaped ring illumination and an image pick-up device for image-picking up the end face illuminated by the illuminating device;
  sequentially moving the hand along an end face of an outer periphery of the glass sheet;
  image-picking up the end face of the glass sheet;
  sequentially processing the image signal acquired by an image processing device, and
  detecting the presence/absence of the defect.

14. The method for detecting a defect on the end face of a glass sheet according to claim 11, comprising:
  inspecting an end face of a side in parallel to a carrying direction of the glass sheet being carried by a first defect inspecting device fixed with respect to a carrying; and
  inspecting an end face of a side perpendicular to the carrying direction of the glass sheet being carried, the second defect inspecting device being movable with respect to the glass sheet,
  wherein the first defect inspecting device and the second inspecting device are provided with respective C-shaped ring illuminations and respective two CCD cameras.

* * * * *